United States Patent
Reischman et al.

(10) Patent No.: US 6,779,505 B2
(45) Date of Patent: Aug. 24, 2004

(54) METHOD OF EMPLOYING INSTRUMENTATION TO EFFICIENTLY MODIFY A LUBRICANT'S FLOW RATE OR PROPERTIES IN AN OPERATING ALL-LOSS LUBRICATING SYSTEM

(75) Inventors: Paul Thomas Reischman, Lambertville, NJ (US); Vincent Mark Carey, Sewell, NJ (US); Kevin John Kelly, Mullica Hill, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/395,972

(22) Filed: Mar. 25, 2003

(65) Prior Publication Data

US 2003/0196632 A1 Oct. 23, 2003

Related U.S. Application Data

(60) Provisional application No. 60/391,319, filed on Jun. 25, 2002, and provisional application No. 60/374,904, filed on Apr. 23, 2002.

(51) Int. Cl.$^7$ .................................................. F01M 1/00
(52) U.S. Cl. .............................. 123/196 R; 123/196 M; 184/6.5
(58) Field of Search .......................... 123/196 R, 196 M; 184/6.5, 6.8, 6.9, 6.21, 6.24, 7.4

(56) References Cited

U.S. PATENT DOCUMENTS 5,754,055 A    5/1998  McAdoo et al. ............ 324/636

*Primary Examiner*—Noah P. Kamen
(74) *Attorney, Agent, or Firm*—Norby L. Foss

(57) ABSTRACT

A method to employ instrumentation to effectuate variation in lubricant flow rate or properties in response to actual engine conditions. Preferably, the present invention provides a method for the in situ monitoring of the lubricating oil's effectiveness in a two-stroke diesel engine by measuring the used lubricant's Fe content and fuel sulfur content with XRF technology and the used lubricant's BN with an IR measurement device, and for efficiently modifying the lubricant's properties and/or flow rate to the equipment in response to the actual wear or corrosion needs of the machinery or engine.

8 Claims, No Drawings

METHOD OF EMPLOYING INSTRUMENTATION TO EFFICIENTLY MODIFY A LUBRICANT'S FLOW RATE OR PROPERTIES IN AN OPERATING ALL-LOSS LUBRICATING SYSTEM

This application claims priority to Provisional Application No. 60/391,319 filed Jun. 25, 2002 and Provisional Application No. 60/374,904 filed Apr. 23, 2002.

FIELD OF THE INVENTION

The present invention relates to a method to employ instrumentation to effectuate variation in lubricant flow rate or properties in response to actual engine conditions.

BACKGROUND OF THE INVENTION

Diesel engines may generally be classified as slow-speed, medium-speed or high-speed engines, with the slow-speed variety being used for the largest, deep draft vessels and in industrial applications. Slow-speed diesel engines are typically direct coupled, direct reversing, two-stroke cycle engines operating in the range of about 57 to 250 rpm and usually run on residual fuels. These engines are of crosshead construction with a diaphragm and stuffing boxes separating the power cylinders from the crankcase to prevent combustion products from entering the crankcase and mixing with the crankcase oil. Medium-speed engines typically operate in the range of 250 to about 1100 rpm and may operate on the four-stroke or two-stroke cycle. These engines are trunk piston design, and many operate on residual fuel as well. They may also operate on distillate fuel containing little or no residua. On deep-sea vessels these engines may be used for propulsion, ancillary applications or both. Slow speed and medium speed marine diesel engines are also extensively used in power plant operations. The present invention is applicable to slow-speed diesel engines in both marine and power plant applications.

Each type of diesel engine employs lubricating oils to lubricate piston rings, cylinder liners, bearings for crank shafts and connecting rods, valve train mechanisms including cams and valve lifters, among other moving members. The lubricant prevents component wear, removes heat, neutralizes and disperses combustion products, prevents rust and corrosion, and prevents sludge formation or deposits.

In low-speed marine crosshead diesel engines, the cylinders and crankcase are lubricated separately, with cylinder lubrication being provided on a once-through basis by means of injection devices that apply cylinder oil to lubricators positioned around the cylinder liner. This is known as an "all-loss" lubrication system. The cylinder oil is typically formulated to provide for good piston ring and cylinder liner wear control, as well as good oxidation and thermal stability, water demulsability, corrosion protection and good antifoam performance. Alkaline detergent additives are also present to neutralize acids formed during the combustion process. Dispersant, antioxidant, antifoam, antiwear and extreme pressure (EP) performance may also be provided by the use of suitable additives.

As engines produce higher power and are operated under more severe conditions, the lubricating oil's required functionality and performance have dramatically increased. These increased performance demands have resulted in a corresponding increase in the lubricant's expense. Lubricants are being made with increasingly sophisticated and expensive base stocks, including wholly synthetic base stocks. In addition, a wide variety of expensive additives, such as dispersants, detergents, antiwear agents, friction reducing agents, viscosity improvers, viscosity thickeners, metal passivators, acid sequestering agents and antioxidants are incorporated into the lubricants to meet functional demands.

Traditionally in Marine Diesel two stroke engines, the lubricant flow rate to the cylinder liner remained constant, or may have varied with respect to engine RPM. Early suggested improvements included setting this constant flow rate as a function of the sulfur content of the bulk bunker fuel taken as a one-time measurement before embarkation.

Studies have demonstrated that to achieve the bare minimum lubrication protection required for a two-stroke crosshead engine, lubricant flow should be modified in response to the prevailing engine operating and fuel conditions. See S. N. Yoo, O. S. Kwon, C. R. Son, "Service Experience of the Largest Diesel Engine Power Plant with Hyundai—MAN B&W 12K90MS-S Engines", *Proceedings of the 27<sup>th</sup> International Congress of Combustion Engines*, p. 160, 2001. DE 10112691.3 incorporated this method by suggesting a near real-time variation of the feed rate of the lubricant to the cylinder liner in response to a real-time or near real time measurement of the sulfur content of the fuel entering the cylinder, or parameters which varied due to this sulfur content (eg. Wear, Fe content in the used lubricant, BN of the used lubricant).

The current inventors, in co-pending application U.S. Ser. No. 60/361376 Feb. 6, 2002 (herein incorporated by reference), improved upon all previous methods by demonstrating an apparatus and method for varying the properties of the lubricant itself in response to any engine condition of concern.

One major inefficiency of DE 10112691.3 is that it did not teach any possible means to obtain these measurements. Indeed, this should not have been unexpected; most devices used to measure used lubricant Fe content and BN did not produce results in near real-time or were too bulky to be included on an operating marine diesel two stroke engine. Similarly, the '691 application neither provided nor suggested a method to actually measure the sulfur content of the fuel in a real-time or near real-time mode However, in developing their invention noted in the above co-pending application, the inventors also discovered a combination of instrumentation that would allow them to efficiently employ their invention. That instrument combination applies as well to an invention that only varied the feed rate of the lubricant to the cylinder liner. It is the object of the present invention to present a combination of instrumentation that will permit both their invention, and that suggested by DE 10112691.3, to effectively operate.

SUMMARY OF THE INVENTION

The present invention relates to a process of employing instrumentation for implementing the near real time varying of an "all loss" diesel engine's lubricating oil's properties or flow rate in response to actual engine lubrication requirements. Preferably, the present invention provides a method for the in situ monitoring of the lubricating oil's effectiveness in a diesel engine by measuring the Fe content of the used lubricant with miniaturized XRF technology, the actual fuel sulfur content using miniaturized XRF technology and the used lubricant's BN with an IR measurement device, and for modifying the lubricant's properties and/or flow rate in response to the actual wear or corrosion, or other needs of the machinery or engine. More preferably, the present invention is directed to the use of these instruments in a system that varies the feed rate or lubricant properties in a two-stroke crosshead diesel engine.

DETAILED DESCRIPTION

The increased performance demands of modern diesel engines have resulted in their mounting sophistication, complexity and sensitivity. In response, cylinder oils have also become more advanced by utilizing more complex base stocks and additives. However, such innovations also provoke higher costs in both the base stocks and the additives.

The engine condition parameter of interest, such as wear, deposits or corrosion, may be measured directly or may be predicted from other engine, used lube oil or fuel parameters. As a non-limiting example, the wear of a component of interest could be directly measured by determining the metal content in metal or metal oxide particles present in the scrape down lubricant from the cylinder liner. In the alternative, wear may also be predicted from other parameters. For example, research has shown that cylinder wear in a two-stroke diesel engine may be accurately predicted from the sulfur content of the fuel, the load on the engine, and the total base number ("TBN") of the lubricant entering the cylinder. See Vince Carey and J. Fogarty, "Key Parameters in Cylinder Oil Performance and Crosshead Diesel Lubrication", *Proceedings of the 21st International Congress of Combustion Engines*, p. D63, 1995, incorporated herein by reference. Thus, the wear of the cylinder may be measured directly or accurately predicted from other parameters.

X-ray Fluorescence spectroscopy ("XRF") analysis began with Barkla and Sadler in 1908 with their recognition that materials do not merely scatter X-ray radiation but modify it thus yielding "characteristic rays". Barkla, C. G., Sadler, C. A. *Philos. Mag.*, 1908, 16, 550. Others showed that the characteristic rays were related to atomic number, i.e. they could be used to identify elements such as iron. In 1948, Friedman and Birks of the U.S. Naval Research Laboratory pioneered the first electronic detection for XRF by replacing photographic film with a Geiger counter. Gilfrich, J. V. *X-Ray Spectrum.*, 2001, 30, 203–211. That innovation paved the way for quantitative XRF measurement.

Since that time, detectors, windows, X-ray sources, algorithms to account for matrix effects, computing power, etc. have improved significantly. In 1983 Sanders, et al. from the Pacific Northwest Laboratory demonstrated that metals in unweighed standard petroleum fuel oil samples could be measured with high accuracy using XRF. Sanders, R. W., Olsen, K. B., Welmer, W. C., Nielson, K. K. *Anal. Chem.*, 1983, 65, 1911–1914. Only recently, Wilson, et al. have reported the use of XRF spectrometers as in-line sensors for monitoring liquids. Wilson, B. W., Price, L. S. *Lubrication and Fluid Power*, Aug. 16–19, 2000.

Although Wilson recognized that the miniaturized XRF instruments were useful to replace used oil analysis in predicting industrial component failure, the present inventors realized from their work on co-pending invention U.S. Ser. No. 60/361776 filed Feb. 26, 2002, that the XRF detectors could be employed to modify the lubricant flow rate or physical or chemical properties thus controlling engine wear or other engine parameters of interest. Of course, this instrumentation package could be extended to control parameters in any component employing a lubricant.

Wilson concluded that actual wear conditions could be determined long after the fact by using XRF to measure the iron content of the used oil samples. However, the present inventors recognized that the real-time wear of the cylinder liner could be measured with in-line XRF detectors. Moreover, the current inventors recognized a novel use for in-line or on-line XRF sensors in that the measurement of sulfur in the fuel oil being burned could be accurately determined in real-time or near real-time. Thus, the same type of sensor could monitor two critical elements of determining the actual wear conditions of the engine and adjusting the lubricant's flow and properties to correct for that wear.

A distinct advantage of this approach is that the sulfur level of the fuel-in-use is known. Sulfur content does not have to be calculated or estimated which is a particularly difficult problem for blended fuels from different bunkerings or when switching from one fuel-in-storage to another. Current practice is to collect fuel samples as they are being bunkered into storage tanks and to send them to a laboratory for analysis. The results are received a few days later. Use of an in-line or on-line device to measure sulfur eliminates the guesswork, and allows for the optimization of the lube oil feed rate and/or composition even when the fuel sulfur level varies significantly. Even though DE 10112691.3 desired that fuel sulfur levels be determined in real-time or near real-time, only the present invention provides a practical method of making that determination.

Likewise, the inventors discovered a unique in-line real time or near real time method of measuring the BN of a used lubricating oil using an IR measurement device as detailed in copending application U.S. Ser. No. 60/361375 filed on Feb. 26, 2002 (herein incorporated by reference). The inventors determined a specific range of the IR spectrum and developed mathematical models relating the peak of this spectrum range to the base line of this range that accurately determined either the BN of the used lubricant, or the change of BN of a used lubricant.

The use of a miniaturized XRF technology independently or combined with the BN/IR technology will improve the efficiency of a system varying the feed rate or properties of a lubricant entering a cylinder liner in a two-stroke diesel engine.

The instrumentation set of this invention may be used singly or in any combination. A preferred method is to use both sensors to vary the feed rate or lubricant properties. Given this solid foundation, one of ordinary skill in the art could easily consider other instruments to add onto this set of instrumentation. Also, it is clear that this instrumentation could apply to a recirculating lubricant system as described by the inventors in their co-pending application U.S. Ser. No. 60/360087 filed Feb. 26, 2002 (which is herein incorporated by reference)

What is claimed is:

1. A method for the modification of a system's base lubricant's flow rate and/or properties during engine operation comprising:
    a) Regularly monitoring, directly or indirectly, one or more engine condition parameters in an engine with one or more instruments selected from the group comprising XRF or BN measurement with IR spectra
    b) Calculating from said engine condition parameters an amount to vary the feed rate or modify the properties of the base lubricant to the engine
    c) Varying the feed rate or modifying the properties of the lubricant.

2. A method as in claim 1 wherein said engine condition parameters is one or more parameters selected from the group comprising lubricant iron content, fuel sulfur content and lubricant Total Base number.

3. A method as in claim 1 where said engine is an all-loss lubricating system.

4. A method as in claim 1 where said engine is a recirculating lubrication engine.

5. A method as in claim 3 where said engine is a two-stroke diesel engine.

6. A method as in claim 5 wherein said two-stroke diesel engine is a crosshead said two-stroke diesel engine.

7. A method as in claim 3 wherein the method is applied to a marine or industrial diesel engine.

8. A method as in claim 3 where said engine is a two-stroke or four-stroke internal combustion engine.

* * * * *